United States Patent [19]

Schultz

[11] Patent Number: 5,367,164

[45] Date of Patent: Nov. 22, 1994

[54] AUTOMATED PYROLYZER METHOD AND APPARATUS

[75] Inventor: Gary A. Schultz, Lansdale, Pa.

[73] Assignee: Rohm and Haas Company, Philadelphia, Pa.

[21] Appl. No.: 76,594

[22] Filed: Jun. 14, 1993

[51] Int. Cl.⁵ .............................................. H01J 49/04
[52] U.S. Cl. ....................................... 250/288; 422/78
[58] Field of Search ............... 250/288, 288 A; 422/78

[56] References Cited

U.S. PATENT DOCUMENTS

| | | | |
|---|---|---|---|
| 4,408,125 | 10/1993 | Meuzelaar | 250/288 |
| 5,240,604 | 8/1993 | Cortes et al. | 422/78 |

OTHER PUBLICATIONS

HP7673 Automatic Sampler Operating Manual, Nov. 1991, pp. 1-2, 1-7, 3-28, 3-40, 3-40a, 4-4, 4-10, 4-18.
Bulletin PB1000 of CDS Analytical Inc.
Publication 5000246 of SGE Int'l. Pty. Ltd.

*Primary Examiner*—Jack I. Berman
*Attorney, Agent, or Firm*—Michael B. Fein

[57] ABSTRACT

An apparatus for pyrolyzing a sample prior to analysis by a gas chromatograph or a mass spectrometer comprising an insertion probe for bearing said sample, a reaction chamber which is mounted to the insertion probe so as to encompass the sample, said insertion probe having a ribbon for depositing said sample and maintaining said sample during a pyrolysis, said insertion probe being removable from said reaction chamber, means for rapidly heating said sample so as to pyrolyze said sample, and an outlet from said reaction chamber to a gas chromatograph or a mass spectrometer; the improvement comprising: means for automatically depositing said sample onto said ribbon while said insertion probe is in said reaction chamber. A method for pyrolyzing samples using said apparatus is also disclosed.

4 Claims, 1 Drawing Sheet

AUTOMATED PYROLYZER METHOD AND APPARATUS

BACKGROUND OF THE INVENTION

1. Field of the Invention

This invention relates to apparatus and methods of analyzing chemical samples, particularly pyrolyzing chemical samples prior to gas chromatography and/or mass spectroscopy.

2. Description of the Prior Art

The use of pyrolysis apparatus to pyrolyze chemical samples prior to analysis by a mass spectrometer is well known. Meuzelaar, U.S. Pat. No. 4,408,125, shows modular pyrolysis inlets and methods of pyrolyzing. Publication No. 5000246 of SGE International Pty. Ltd., entitled Pyrojector Series II shows a continuous mode micro furnace pyrolyzing unit which is a furnace with sample introduction means for both liquid and solid samples. Bulletin-PB1000 of CDS Analytical Inc. shows Pyroprobe Models 1000 and 2000 and ribbon elements.

Frequently autoinjectors such as Hewlett Packard Model 7673B are used to automatically insert samples for subsequent analysis by a gas chromatograph or a mass spectrometer.

The prior art procedure is to manually deposit a sample to be analyzed on a ribbon of a pyroprobe, insert the probe in a pyrolysis chamber, turn on the heating system, with the pyrolysis apparatus designed to vent the pyrolysis product directly to a gas chromatography apparatus.

SUMMARY OF THE INVENTION

It has become an object to provide an improved pyrolysis apparatus which allows for more efficient and accurate pyrolysis for gas chromatography and/or mass spectroscopy (GC/MS). Another object is to provide a more efficient and accurate method and apparatus for pyrolyzing chemical samples for subsequent GC/MS.

These objects, and others which will become apparent from the following disclosure, are achieved by the present invention which comprises in one aspect an apparatus for pyrolyzing a sample prior to analysis by a gas chromatograph or a mass spectrometer, said apparatus comprising an insertion probe for bearing said sample, a reaction chamber in which is mounted the insertion probe so as to encompass the sample, said insertion probe having a ribbon for depositing said sample and maintaining said sample during pyrolysis, said insertion probe being removable from said reaction chamber, means for rapidly heating said sample so as to pyrolyze said sample, and an outlet from said reaction chamber to a gas chromatograph or a mass spectrometer; the improvement comprising:

means for automatically depositing said sample onto said ribbon while said insertion probe is in said reaction chamber.

In another aspect the invention comprises a process of pyrolyzing a sample prior to analysis by a gas chromatograph or a mass spectrometer comprising automatically depositing said sample on a ribbon on an insertion probe for bearing said sample while said insertion probe is mounted in a reaction chamber, rapidly heating said sample so as to pyrolyze said sample, removing or sweeping the pyrolysis products of said sample through an outlet to a gas chromatograph or a mass spectrometer.

DETAILED DESCRIPTION OF THE INVENTION AND THE PREFERRED EMBODIMENTS

Figure 1:
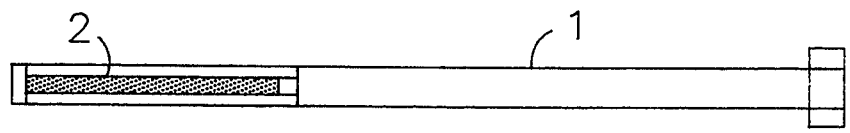
FIG. 1 is a top perspective view, partially in section, of a pyrolysis probe having a ribbon for deposit of sample.
Figure 2:
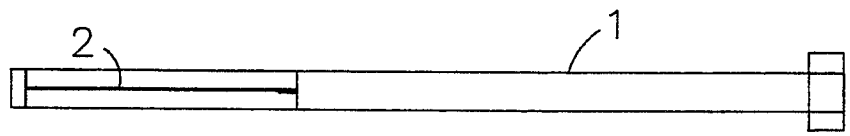
FIG. 2 is a side perspective view of the probe illustrated in FIG. 1, also partially in section.
Figure 3:
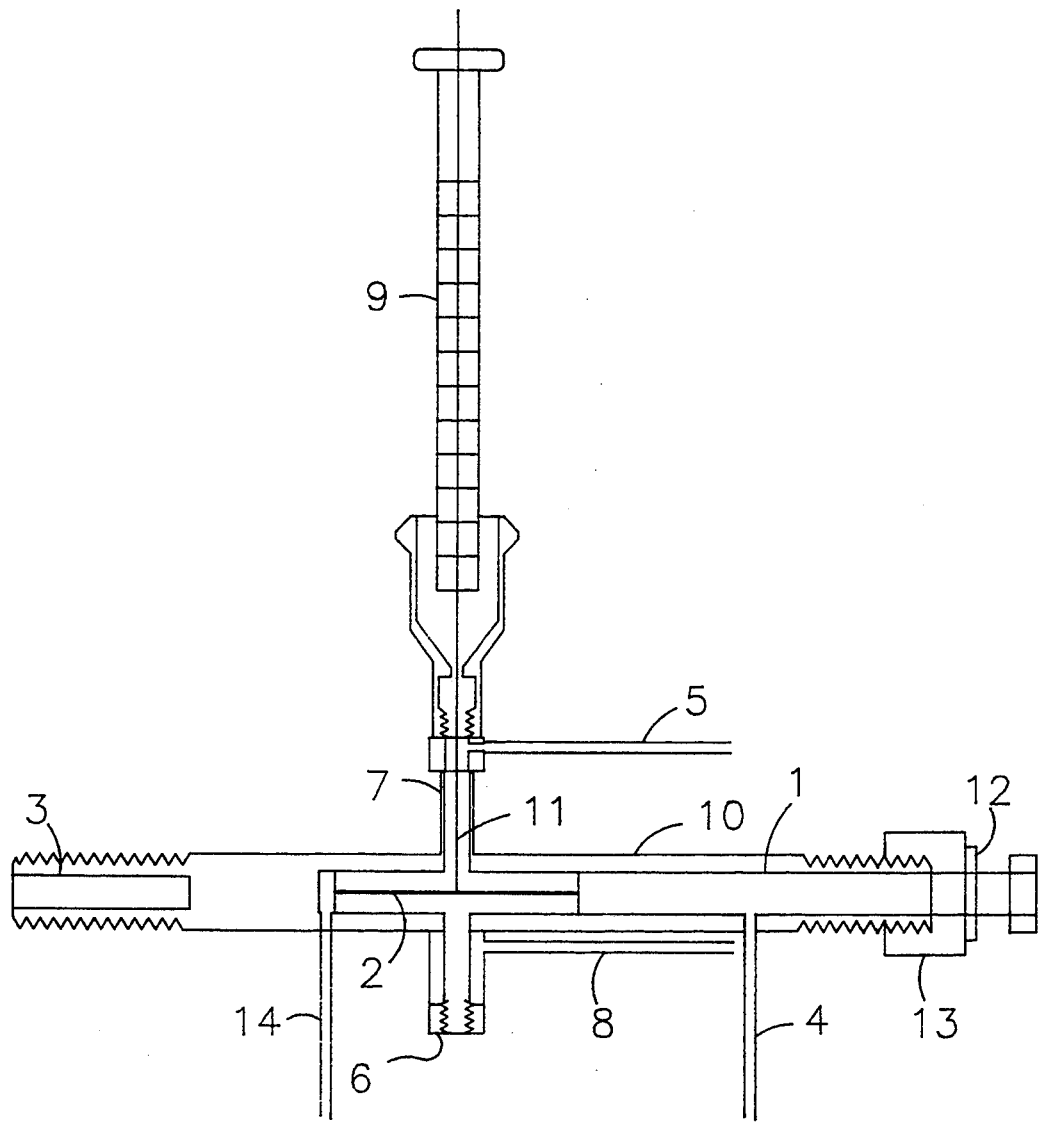
FIG. 3 is a side perspective view of a portion of the apparatus of the invention, also partially in section.

Referring to the drawings, a pyroprobe 1 having a ribbon 2 (preferably platinum) is inserted in a pyrolysis chamber 10. The ribbon is in a relatively horizontal position and under a novel plenum 7 through which sample is deposited via syringe 9. According to the present invention, the probe is not removed during normal operation, which is contrary to the prior art methods. The pyrolysis chamber is heated according to a program by heating element (not shown) wrapped around said pyrolysis chamber 10 and temperature of said pyrolysis chamber 10 measured by thermocouple 3. An automated liquid sampling device (not shown) is programmed to deposit samples via syringe 9 at inlet 7, and needle 11 onto ribbon 2. Helium input lines 4, 5 and 14, preferably about 1/16" stainless steel, carry helium gas which is vented at the programmed time along with volatile pyrolysis products through outlet 6 to a gas chromatograph or mass spectrometer (not shown). Helium gas is vented through output line 8. Helium gas carries sample out sample output plenum 6 after it is pyrolyzed.

As will be readily apparent to those skilled in this art, this invention provides an apparatus for pyrolyzing a sample prior to analysis by a gas chromatograph or a mass spectrometer comprising an insertion probe 1 for bearing said sample, a reaction chamber 10 which is mounted to the insertion probe 1 so as to encompass the sample, said insertion probe having a ribbon 2 for depositing said sample and maintaining said sample during pyrolysis, said insertion probe 1 being removable from said reaction chamber, means for rapidly heating said sample so as to pyrolyze said sample, and an outlet 6 from said reaction chamber 10 to a gas chromatograph or a mass spectrometer; the improvement comprising:

means for automatically depositing said sample onto said ribbon while said insertion probe is in said reaction chamber.

Preferably the device comprises a syringe 9 for depositing a solution of said sample on said ribbon 2, said device being mounted above said reaction chamber 10 and connected to an injection port 7 of said reaction chamber 10 so that said syringe 9 is positioned to deposit solution directly onto said ribbon 2 while said insertion probe 1 is mounted in said reaction chamber 10.

In operation, the device is programmed to automatically deposit appropriate quantities of sample solution during a time while said reaction chamber is programmed to maintain an ambient temperature, and the apparatus is also programmed to raise the temperature of the reaction chamber slowly so as to volatilize the solvent of said sample solution, and to rapidly raise the temperature of said ribbon so as to pyrolyze the remaining sample deposited on said ribbon, and thereafter the helium gas carry the volatile pyrolysis products to a gas chromatograph or a mass spectrometer, following which the temperature of the reaction chamber is allowed to lower again to ambient temperature at which time another solution of sample is automatically deposited on said ribbon.

Preferably, the apparatus is programmed to raise the temperature of said reaction chamber at a rate of about 2° to about 30° C./minute, and to raise the temperature of said ribbon at a rate of about 0.1° C./minute to about 20° C./milli-second. Most preferably said reaction chamber temperature is raised at a rate of about 30° C./minute and said temperature of said ribbon is raised at a rate of about 20° C./milli-second.

In a preferred embodiment, a Hewlett Packard model 7673B autoinjector is mounted on an elevated platform above a novel pyrolysis chamber in which a CDS Model 2000 pyroprobe equipped with a ribbon element is mounted by use of the threaded connectors, and sealed with an O-ring 12 and Swagelok nut 13. The pyrolysis chamber is connected to a GC/MS. The pyrolysis chamber is specially adapted with a plenum above the location of the ribbon when inserted in the furnace, and said plenum is adapted to fit the section of the automated liquid sampling device that controls the syringe used to deposit sample solutions onto ribbon of pyroprobe.

While the invention has been described and exemplified in detail herein, various modifications, alternatives, and improvements should become readily apparent to those skilled in the art without departing from the spirit and scope of the invention.

I claim:

1. In an apparatus for pyrolyzing a sample prior to analysis by a gas chromatograph or a mass spectrometer comprising an insertion probe for bearing said sample, a reaction chamber which is mounted to the insertion probe so as to encompass the sample, said insertion probe having a ribbon for depositing said sample and maintaining said sample during pyrolysis, said insertion probe being removable from said reaction chamber, means for rapidly heating said sample so as to pyrolyze said sample, and an outlet from said reaction chamber to a gas chromatograph or a mass spectrometer; the improvement comprising:

means for automatically depositing a series of samples onto said ribbon while said insertion probe is in said reaction chamber, said means including an automated liquid sampling device which comprises a syringe for depositing discrete amounts of solutions of said samples on said ribbon, said device being mounted above said reaction chamber and connected to an injection port of said reaction chamber so that said syringe is positioned to deposit solution directly onto said ribbon while said insertion probe is mounted in said reaction chamber.

2. Apparatus according to claim 1 wherein said device is programmed to automatically deposit appropriate quantities of sample solution during a time while said reaction chamber is programmed to maintain an ambient temperature, and the apparatus is also programmed to raise the temperature of the reaction chamber slowly so as to volatilize the solvent of said sample solution, and to rapidly raise the temperature of said ribbon so as to pyrolyze the remaining sample deposited on said ribbon, and thereafter helium gas carry the volatile pyrolysis products to a gas chromatograph or a mass spectometer, following which the temperature of said reaction chamber is allowed to lower again to ambient temperature at which time another solution of sample is automatically deposited on said ribbon.

3. Apparatus according to claim 2 wherein said apparatus is programmed to raise the temperature of said reaction chamber at a rate of about 2° to about 30° C./minute, and to rapidly raise the temperature of said ribbon at a rate of about 0.1° C./minute to about 20° C./millisecond.

4. Process of pyrolyzing a sample prior to analysis by a gas chromatograph or a mass spectrometer comprising automatically depositing a discrete amount of a solution of said sample on a ribbon on an insertion probe for bearing said sample while said insertion probe is mounted in a reaction chamber, rapidly heating said sample so as to pyrolyze said sample, removing the pyrolysis product of said sample through an outlet to a gas chromatograph or a mass spectrometer, and then automatically repeating said depositing a discrete amount step with another solution of sample.

* * * * *